United States Patent
Hamad et al.

(10) Patent No.: US 6,684,167 B2
(45) Date of Patent: Jan. 27, 2004

(54) METHOD AND APPARATUS FOR MEASURING ENERGY CONSUMED DURING PLASTIC DEFORMATION IN MULTI-PLY BOARD SYSTEMS

(75) Inventors: Wadood Hamad, Mahwah, NJ (US); Robert A. Hulbert, Highland, NY (US); Henry J. Kent, Bloomingburg, NY (US)

(73) Assignee: International Paper Company, Stamford, CT (US)

( * ) Notice: Subject to any disclaimer, the term of this patent is extended or adjusted under 35 U.S.C. 154(b) by 406 days.

(21) Appl. No.: 09/855,325

(22) Filed: May 15, 2001

(65) Prior Publication Data

US 2002/0193912 A1 Dec. 19, 2002

(51) Int. Cl.[7] .............................. G01L 1/04; G01N 3/20
(52) U.S. Cl. .............................. 702/42; 73/159; 73/847; 73/849; 73/851
(58) Field of Search .............................. 702/41, 42, 43, 702/44; 73/835, 847, 849–852; 428/853, 34.5, 112; 425/104; 700/108, 110, 291, 295

(56) References Cited

U.S. PATENT DOCUMENTS

| | | | |
|---|---|---|---|
| 1,612,415 A | 12/1926 | Carlson | 73/853 |
| 1,951,908 A | 3/1934 | Hayford | 73/812 |
| 2,462,826 A | 2/1949 | Waard et al. | 73/853 |
| 2,473,841 A | 6/1949 | Anderson | 73/853 |
| 4,958,522 A | 9/1990 | McKinlay | 73/847 |
| 5,199,305 A | 4/1993 | Smith et al. | 73/851 |
| 5,419,202 A | 5/1995 | Howard et al. | 73/849 |
| 5,566,570 A | 10/1996 | Hankel et al. | 73/159 |
| 5,574,227 A | 11/1996 | Allan | 73/849 |
| 5,606,134 A | 2/1997 | Stieber | 73/849 |
| 5,737,238 A | 4/1998 | Mouradian et al. | 700/110 |
| 6,050,149 A | 4/2000 | Yoshizawa | 73/849 |
| 6,158,287 A | 12/2000 | Satake et al. | 73/835 |

OTHER PUBLICATIONS

M. Ferahi, T. Uesaka and D. Lord; Finite Element Analysis of Scoring–Cracking in Corrugated Board, 1988 Progress in Paper Physics: A Seminar, Aug. 1998.
W.J. Whitsitt and R.C. McKee; An Investigation of Linerboard Cracking, Int. of Paper Chemistry, Appleton, Wisconsin, Dec. 1966.

*Primary Examiner*—John Barlow
*Assistant Examiner*—John Le
(74) *Attorney, Agent, or Firm*—Ostrager Chong & Flaherty LLP

(57) ABSTRACT

A method and an apparatus for predicting a score-line cracking propensity of a multi-ply substrate. The method includes the steps of: bending the multi-ply substrate; acquiring tensile load data from the multi-ply substrate during bending; and computing a material property of a top ply of the multi-ply substrate based on the acquired tensile load data. The material property must show a strong correlation to the score-line cracking propensity of the multi-ply substrate. The material property which is computed is the energy consumed in plastic deformation of the top ply during the fracture process. The measurement results can be used to predict score-line cracking propensity in multi-ply board systems, such as multi-ply paperboard.

28 Claims, 7 Drawing Sheets

US 6,684,167 B2

METHOD AND APPARATUS FOR MEASURING ENERGY CONSUMED DURING PLASTIC DEFORMATION IN MULTI-PLY BOARD SYSTEMS

FIELD OF THE INVENTION

This invention generally relates to the manufacture of paperboard products. In particular, the invention relates to methods and apparatus for predicting score-line cracking propensity in paperboard products having multiple plies.

BACKGROUND OF THE INVENTION

There have been available few tests for evaluating score-line cracking, for instance, the score cracking angle test disclosed by Whitsitt and McKee in "Investigation of Improved Device for Evaluating the Cracking Potential of Linerboard," Institute of Paper Chemistry Summary Report, Project No. 1108-29 (1996). This test, first developed at the Institute of Paper Chemistry, fails to either measure a fundamental material property, or detect damage in a single ply. No meaningful correlations have thus been found over the years to score-line cracking performance in the field.

A recent test, disclosed by J. Gonzalez in "Score Cracking in Linerboard," M. S. Dissertation (No. 6190-Research), Institute of Paper Science and Technology, Georgia (2000), is not so much a predictive test, but rather is a set-up that attempts to replicate, rather poorly, scoring. It does not scientifically measure any board property that may prove to correlate to score-line cracking propensity in the field. The test comprises two motor-driven horizontal metal wheels forming essentially a nip compression. A linerboard sample (25 cm×12 cm), manually folded in half and fed between the flat metal wheels, undergoes a nip-type compressive force. The cracking percent of the folded sample is then measured visually or using a microscope.

Experimental work carried out at International Paper's Corporate Research Center in the period February–May, 2000 has been instrumental in providing insight into the root causes of the propensity for score-line cracking in white-top linerboard (especially 69 lb.). The mechanistic basis for designing a score-line-crack-resistant two-ply linerboard is grounded in three (non-mutually exclusive) functional factors: (1) the ability of the top ply to undergo large plastic (irreversible) deformation prior to failure; (2) the ability of the base ply to compress elastically while the top ply is deforming (plastically); and (3) in order for (1) and (2) to simultaneously apply, the interlaminar (ply) bond must be low enough (but adequate to ensure against delamination) to allow the top ply to "slide" over the base ply. Achieving this requires the development of a testing method capable of predicting plastic deformations, or the fracture toughness, of the top ply alone, and able to correlate such a measurement with score-line cracking propensity in the field.

In materials science and engineering, the term "material" has a precise meaning. It refers to either a pure substance or an alloy that can be approximated as essentially homogeneous in composition. When more than one substance or material are combined, and when this combination has internal structural heterogeneity, the term "composite material" is used. According to this definition, wood fibers may be regarded as composite materials, or, specifically, composite tubes of cellulosic microfibrils embedded in an amorphous matrix of hemicellulose and lignin. Structurally, paper or board is, however, a network. On a microscopic scale, paper or board is a cellulosic network of crossing fibers filled with voids; macroscopically, it could be regarded as a continuum with inherent (micro)cracks and flaws being "smeared out" for the purpose of simplifying analysis. For practical issues related, for instance, to box construction, such as scoring, it may be deemed appropriate that linerboard be dealt with as a continuum whose material properties and structural analysis are determined relying on theories of elasticity and plasticity from the field of solid mechanics. Thus, two-ply linerboard constructs comprise two elastic-plastic sheet-like materials whose properties may be analyzed orthotropically. Safeguarding against, for instance, cracking in the top ply during scoring would necessitate attention principally to: i) the extent of (plastic) deformability in each ply; and ii) inter-ply stresses.

Linear elastic materials load and unload along the same path (see FIG. 1); crack growth in such a material can be represented graphically by the load-displacement curve depicted in FIG. 2. The curve is linear up to the point of crack propagation, and the displacement is zero when the specimen is unloaded. The energy consumed in the fracture process is therefore equivalent to the area enclosed under the curve. The irreversible work consumed during elastic fracture is confined to thin boundary layers along the faces of the propagating crack.

Paper and board, however, are tough, ductile materials (the extent of which depends on furnish composition and papermaking conditions) whose yield stress is low (see FIG. 3). When such a material is strained, it yields not only at the point(s) of crack initiation, but away from these points too. Thus, irreversible deformation is no longer confined to the thin boundary layer along the faces of the propagated crack (as in elastic fracture), but is spread throughout the material. In addition to the work required in the crack tip process zone, significant irreversible work is consumed in the yielded regions away from the crack. It is important to recognize that the plastic deformation outside the fracture process zone is not essential to the process of fracture. Consequences of the plastic flow include curvature in the load-displacement curve on loading, and displacement irreversibilities upon unloading, both in a specimen without a crack (FIG. 3) and a specimen with a crack (FIG. 4).

The work done during loading, given by the area under the load-displacement curve in FIG. 4, represents the combined contribution to fracture and remote flow. These two works are difficult to separate experimentally. However, a methodology is needed to separate the elastic and plastic portions of the fracture energy consumed in deforming the top-ply of two-ply linerboard systems. This methodology should be designed so that the measured plastic contribution of the work done during the fracture process correlates well with predicting the propensity of linerboard to score-line cracking during converting operations.

SUMMARY OF THE INVENTION

The present invention is directed to a method and an apparatus for predicting a score-line cracking propensity of a multi-ply substrate. The method comprises the steps of: bending the multi-ply substrate; acquiring data from the multi-ply substrate during bending; and computing a material property of a top ply of the multi-ply substrate based on the acquired data. The material property must show a strong correlation to the score-line cracking propensity of the multi-ply substrate. In accordance with the preferred embodiment of the invention, the material property which is computed is the energy consumed in plastic deformation of the top ply during the fracture process. The measurement results can be used to predict score-line cracking propensity in multi-ply board systems. In accordance with the preferred embodiment, the substrate is paperboard.

Also in accordance with the preferred embodiment, the apparatus is implemented as a top-ply fracture tester designed to bend a sample of a multi-ply substrate and acquire data during bending from which the plastic energy consumption during the fracture process can be automatically computed. The tester comprises two clamps in which the sample is placed; one of the clamps is fixed, the other rotates the sample around a spindle. When bending the sample, it is under a net tensile force, which is recorded using a load cell. A computer receives inputs from the load cell and from a position detector which detects the position of the rotating clamp during the sample bending operation. The computer is programmed to compute the energy consumed during plastic deformation of the top ply of the multi-ply substrate. This top-ply fracture tester induces fracture in the top ply only, and allows the identification of elastic and plastic regions in a single ply. Score-line cracking resistance essentially emanates from the ability of the sheet to deform plastically (in the top ply).

The test and analysis methods in accordance with the preferred embodiment characterize failure in the outermost ply of a multi-ply linerboard system. The test method specifically measures cracking resistance, and correlates board functionality to field performance (converting operations), by accurately measuring the nonlinear, plastic deformation of the ply, or plastic fracture energy.

In accordance with the teaching of the invention, material changes in the board can be correlated with "damage" phenomena, occurring physically, which are relatively easily detectable. When a two-ply linerboard sample is tested as described above, an operator would visually notice three distinct phenomena taking place at three discrete intervals: (1) the development of a (macro)crack as the sample is bent around the spindle; (2) the opening up of the (macro)crack; and (3) the complete separation of the fibers, just prior to eventual failure and delamination of the top ply from the base ply. These stages are respectively referred to herein by the terms "crack," "gap" and "flap." These stages represent the entire zone of plastic deformation while subjecting the top ply to a net tensile state of stress. Plastic deformation in linerboard is thus characterized by two components: the energy consumed during the transition from crack to gap and that consumed during the transition from gap to flap. Each component, or both, may be optimized to improve certain aspects of the board's ability to deform plastically, and, in turn, resistance to cracking.

In accordance with the preferred method, the operator records the visual detection of the crack, gap and flap by pressing a pre-specified alphanumeric key (on the computer keypad) for each event. The computer is programmed to detect these specific key depressions. Once the test is complete, the computer program computes the (elastic and plastic) energies consumed from inception to failure of the single ply. Generally, the following is determined from a specimen's load-elongation curve: (1) energy consumed during elastic deformation (up to crack initiation); (2) energy consumed during the crack-to-gap transition (the first plastic component); (3) energy consumed during the gap-to-flap transition (second plastic component); and (4) energy consumed during the crack-to-flap transition (total plastic contribution, or sum of energy components (2) and (3)). The computer is also preferably programmed to compute the standard deviations, which may further help indicate two things: operator's precision (the larger the standard deviation, the worse is the operator's accuracy for identifying crack, gap and flap) and sample variability (for instance, the standard deviation tends to be higher for recycle furnishes owing to inherent variability in pulp quality and, hence, mechanical properties of the board).

Thus the top-ply fracture tester disclosed herein enables one to instantaneously obtain a load-displacement curve for each ply of a multi-ply linerboard system, or any similar multi-ply structure. From the individual load-elongation curve, each ply's elastic and plastic components are computed and analyzed. For white-top linerboard, it is shown that the top ply is characterized by a two-component plastic zone of deformation, which are respectively referred to herein as the "crack-to-gap" and the "gap-to-flap" components. An unequivocal correlation has been shown between the energy consumed during the crack-to-flap transition (the whole plastic zone) and the propensity for score-line cracking in the field. The plastic zone characterization also serves as a litmus test, which would be useful for proposing ways to improve the board's mechanical performance under varying papermaking conditions, furnish type and board structural configuration.

DETAILED DESCRIPTION OF THE PREFERRED EMBODIMENTS

In accordance with the preferred embodiment of the invention, a predictive tester for score-line cracking was developed which is able to measure the energy consumed in causing cracks to initiate and propagate in each ply of a multi-ply board. The energy consumption necessarily relates to the ability of the board to deform plastically. The tester achieves this goal by measuring a fundamental material property, which may then be correlated with field performance, i.e., converting operations.

Existing techniques for measuring fracture toughness (the essential work of fracture technique or the J-integral technique) would yield an overall number for the combined board that obfuscates the true fracture toughness value of the single ply. Hence, a measurement as such is rendered unhelpful to predicting, and subsequently minimizing, the cracking propensity of the top ply in a two-ply linerboard.

Figure 1:
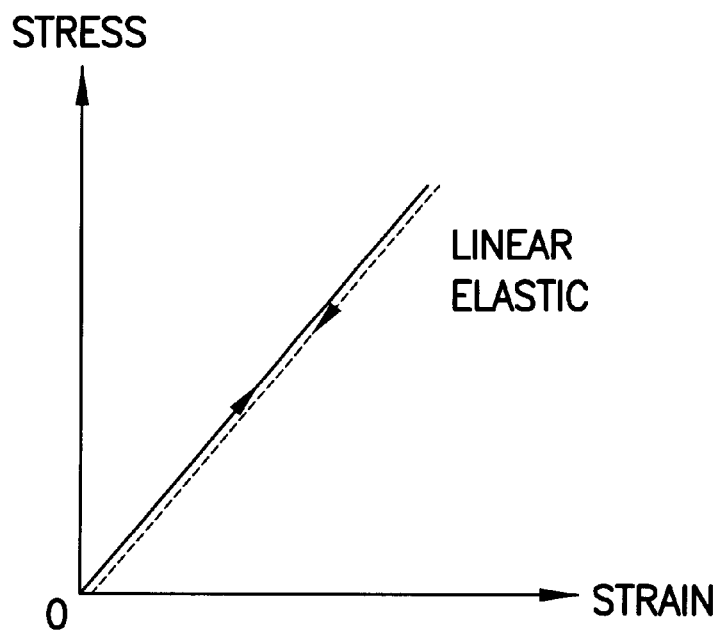
FIG. 1 is a graph showing a stress-strain curve for a linear elastic material.
Figure 2:
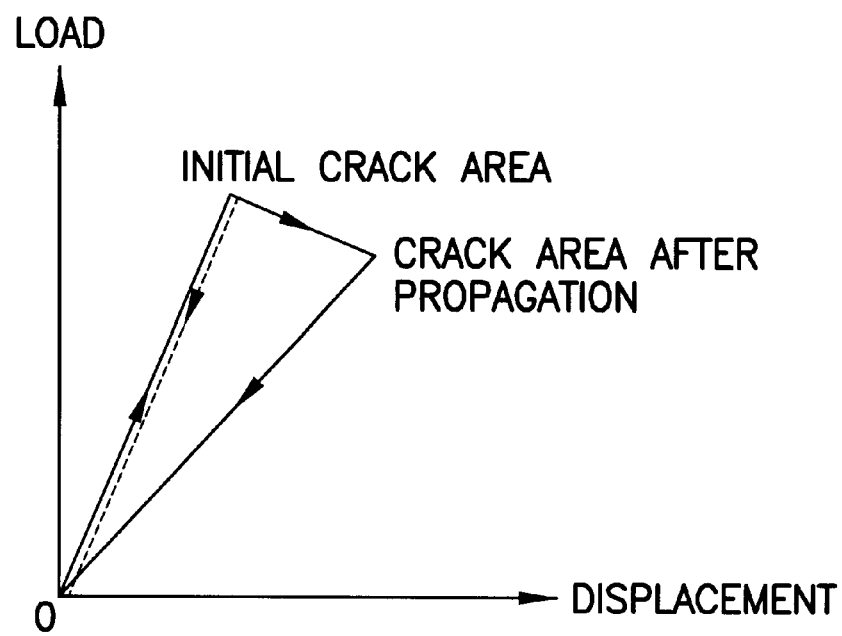
FIG. 2 is a graph showing a load-displacement curve for crack propagation in a linear elastic material.
Figure 3:
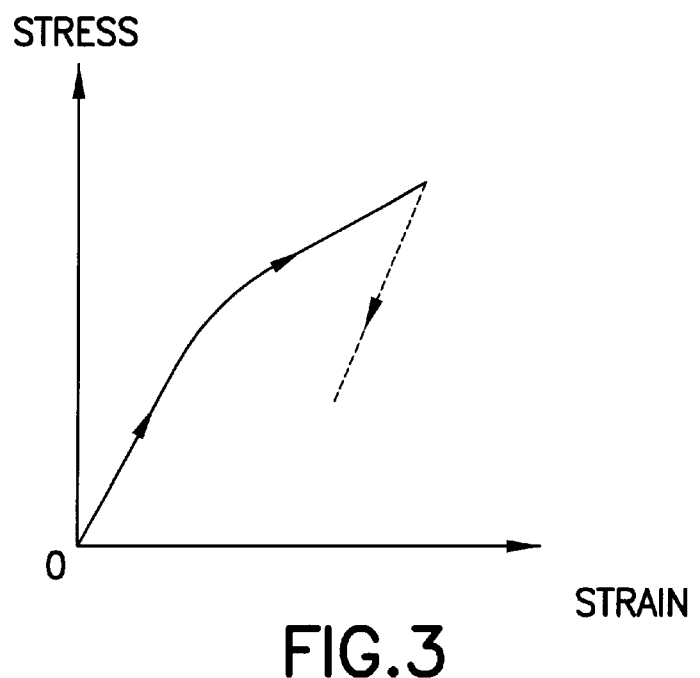
FIG. 3 is a graph showing a stress-strain curve for an elastic-plastic material.
Figure 4:
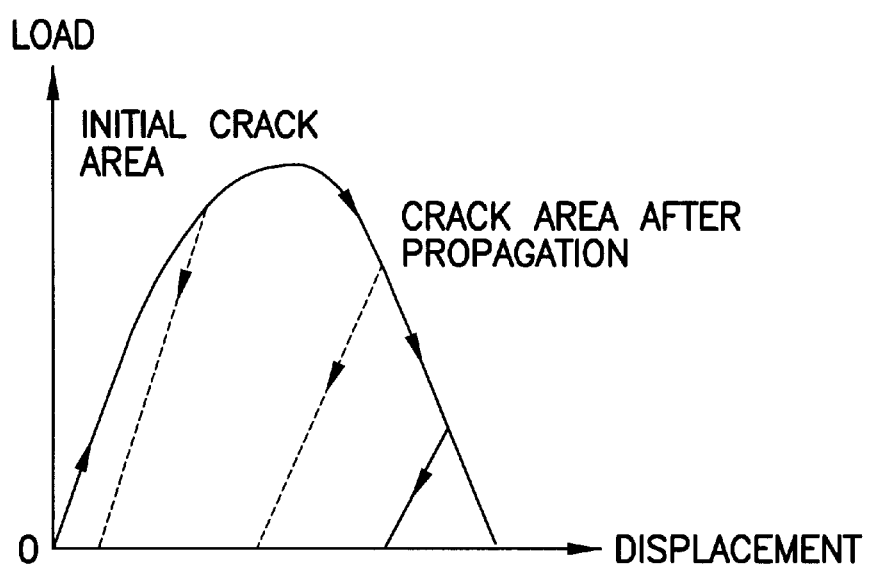
FIG. 4 is a graph showing a load-displacement curve for crack propagation in an elastic-plastic material.
Figure 5:
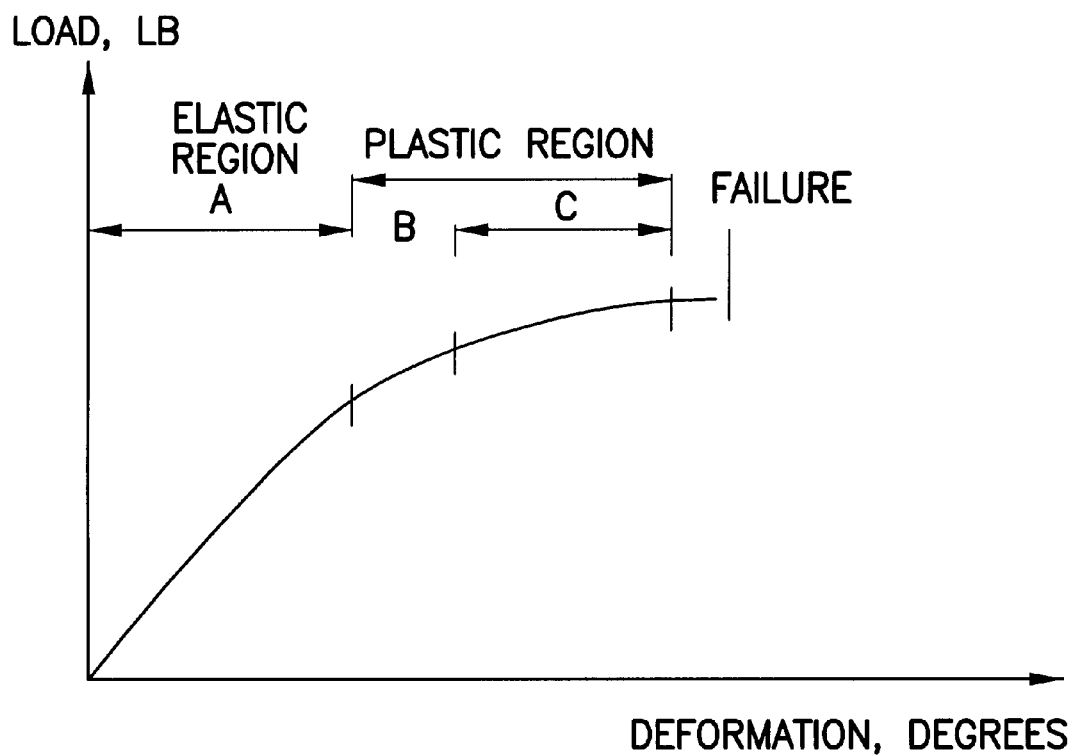
FIG. 5 is a schematic representation of load versus deformation to show the principles of fracture as applied to deforming the top ply in a two-ply linerboard construct: A), the elastic region until crack initiation; B) the crack-to-gap transition; C) the gap-to-flap transition; B+C) crack-to-flap transition.
Figure 6:
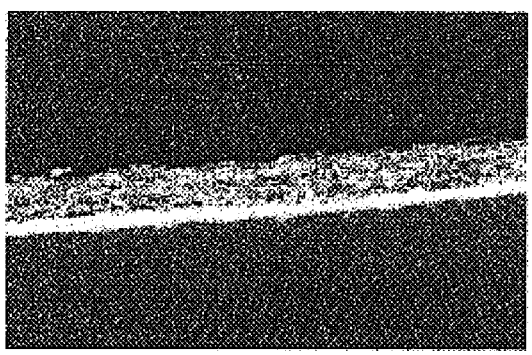
FIGS. 6–9 are photographs showing crack initiation and propagation to failure in the top ply of a two-ply linerboard construction. These side views respectively depict: an intact sample (FIG. 6); crack initiation (FIG. 7); further crack propagation to the gap stage (FIG. 8); and ultimate failure of the top ply, i.e., the flap stage (FIG. 9).
Figure 7:
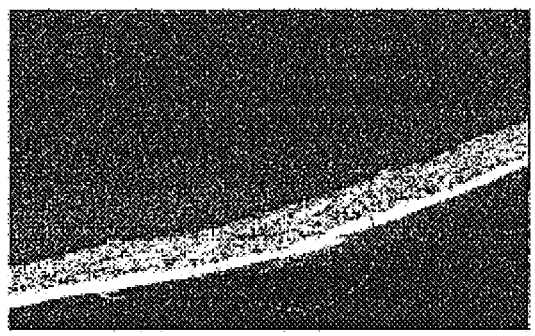
Figure 8:
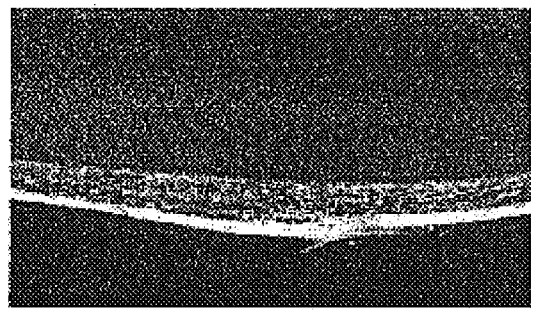
Figure 9:
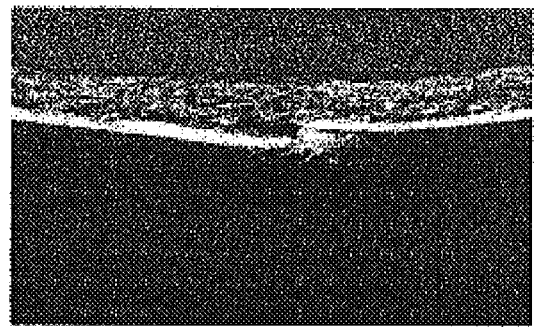

The top-ply fracture tester disclosed herein provides an accurate measure of the energy consumed in deforming the top ply on its own. This capability allows one to investigate score-line cracking phenomena occurring in the top ply of the linerboard. The top-ply fracture tester induces fracture in the top ply only, and allows the identification of elastic and plastic regions in a single ply, as shown in FIG. 5. In the graph shown in FIG. 5, the term "crack" refers to observable discontinuities in the outermost ply under observation; the term "gap" refers to the propagation of macro-cracks leading to their opening up; and the term "flap" refers to the increase in the gap, or crack opening, and ultimate delamination of the ply (under observation) upon further load application. These terms are further illustrated in the photographs presented in FIGS. 6–9, which represent crack initiation and propagation to failure in the top ply of a two-ply linerboard construct. In particular, FIGS. 6–9 are side views which respectively depict: an intact sample (FIG. 6); crack initiation (FIG. 7); further crack propagation to the gap stage (FIG. 8); and (d) ultimate failure of the top ply, i.e., the flap stage (FIG. 9).

The instrument in accordance with the preferred embodiment is programmed to report each of three values for each replicate and then give the average and standard deviation of each value after the last replicate is run. The reported values are the following: (1) The area under the stress-strain curve up to the point of crack initiation in the outermost ply. The area under the stress-strain curve represents the energy consumed, in this case up to crack initiation. (2) The area under the stress-strain curve from the crack to the gap. This area represents the energy consumed during the process following crack initiation and before the inception of gap formation, or crack opening. (3) The area under the curve from the gap to the flap. This area represents the energy consumed during the process of gap formation, or crack opening, and ultimate delamination within the same ply.

Figure 10:
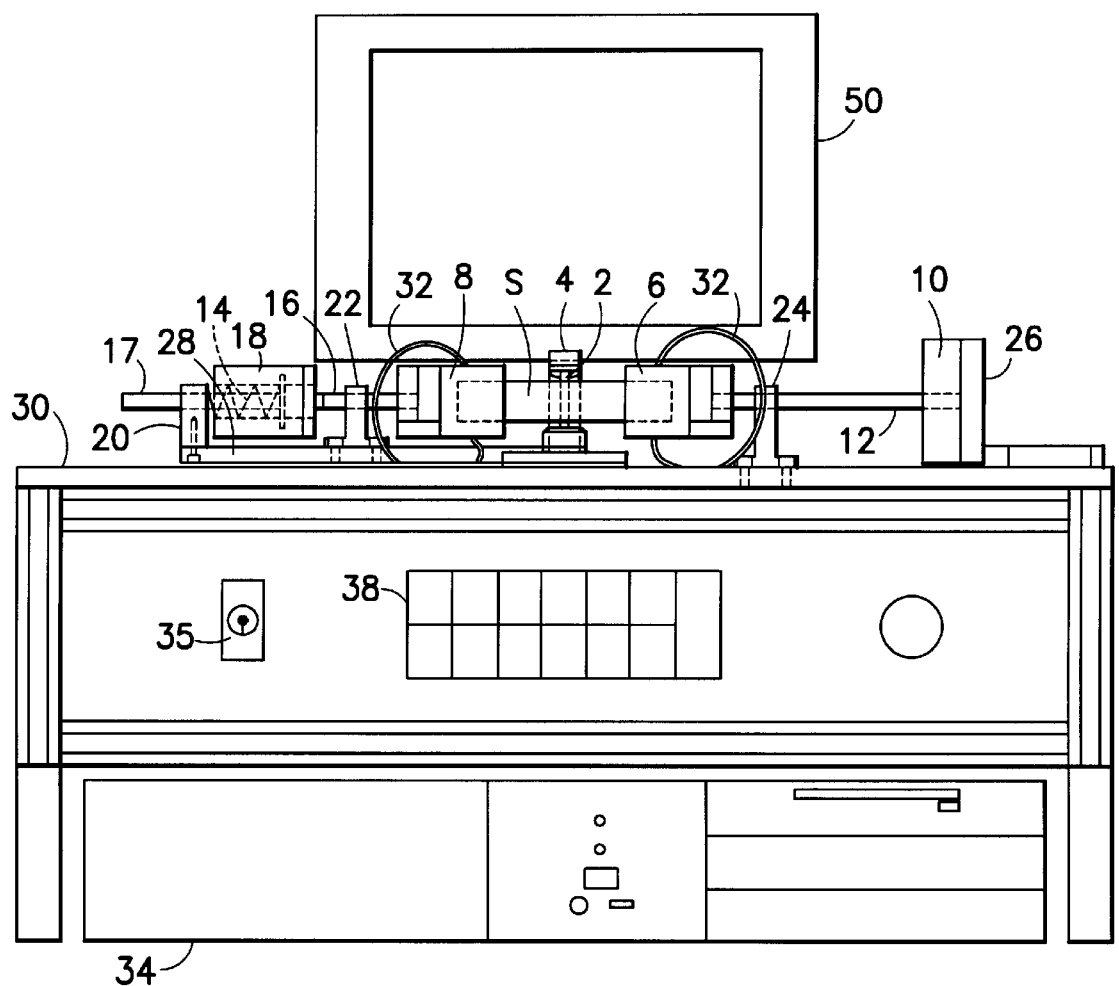
FIG. 10 is a schematic showing a front view of a top-ply fracture tester in accordance with the preferred embodiment of the invention.
Figure 11:
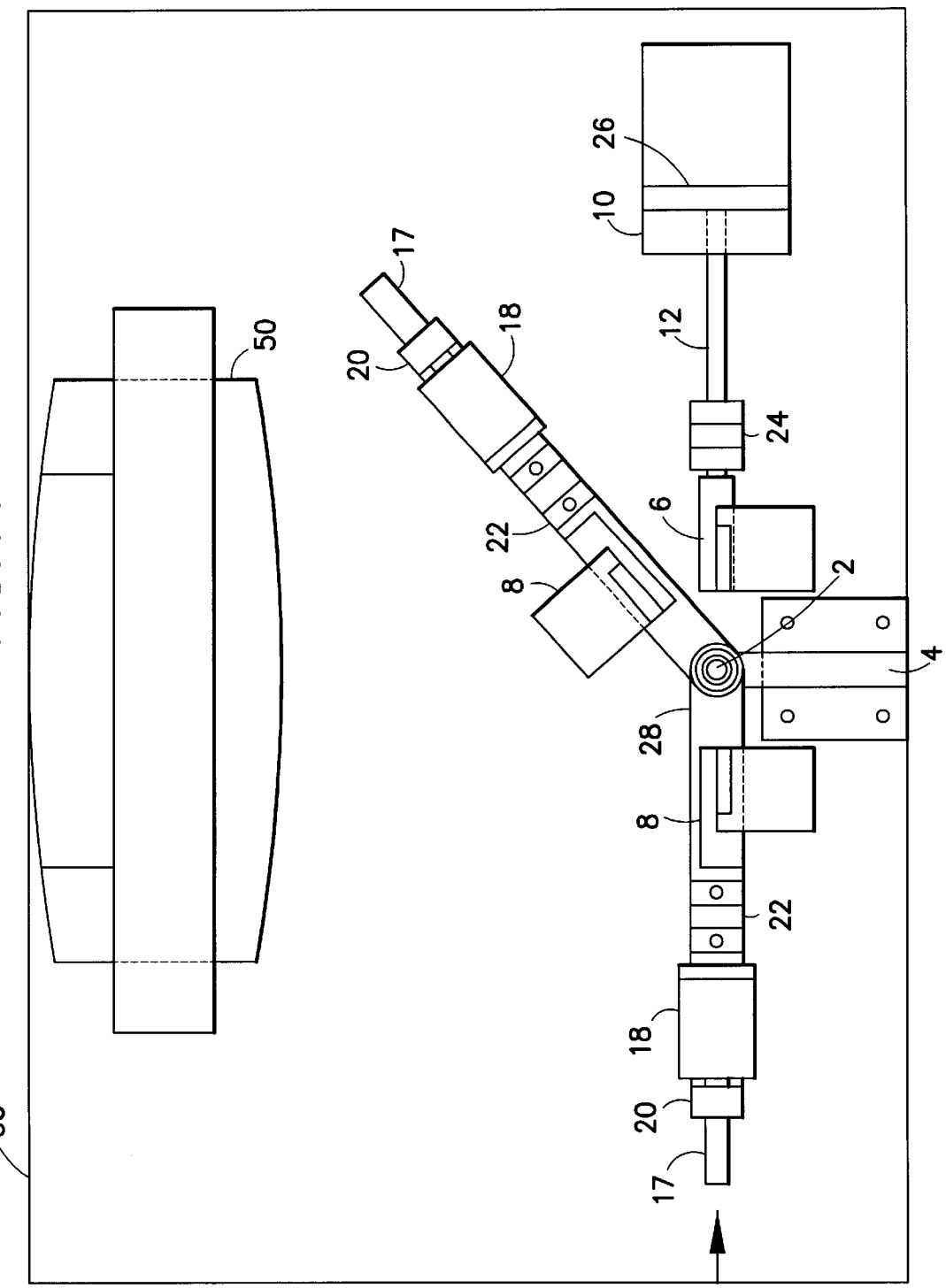
FIG. 11 is a schematic showing a top view of the top-ply fracture tester in accordance with the preferred embodiment of the invention. The rotating arm is shown in its initial and final positions.
Figure 12:
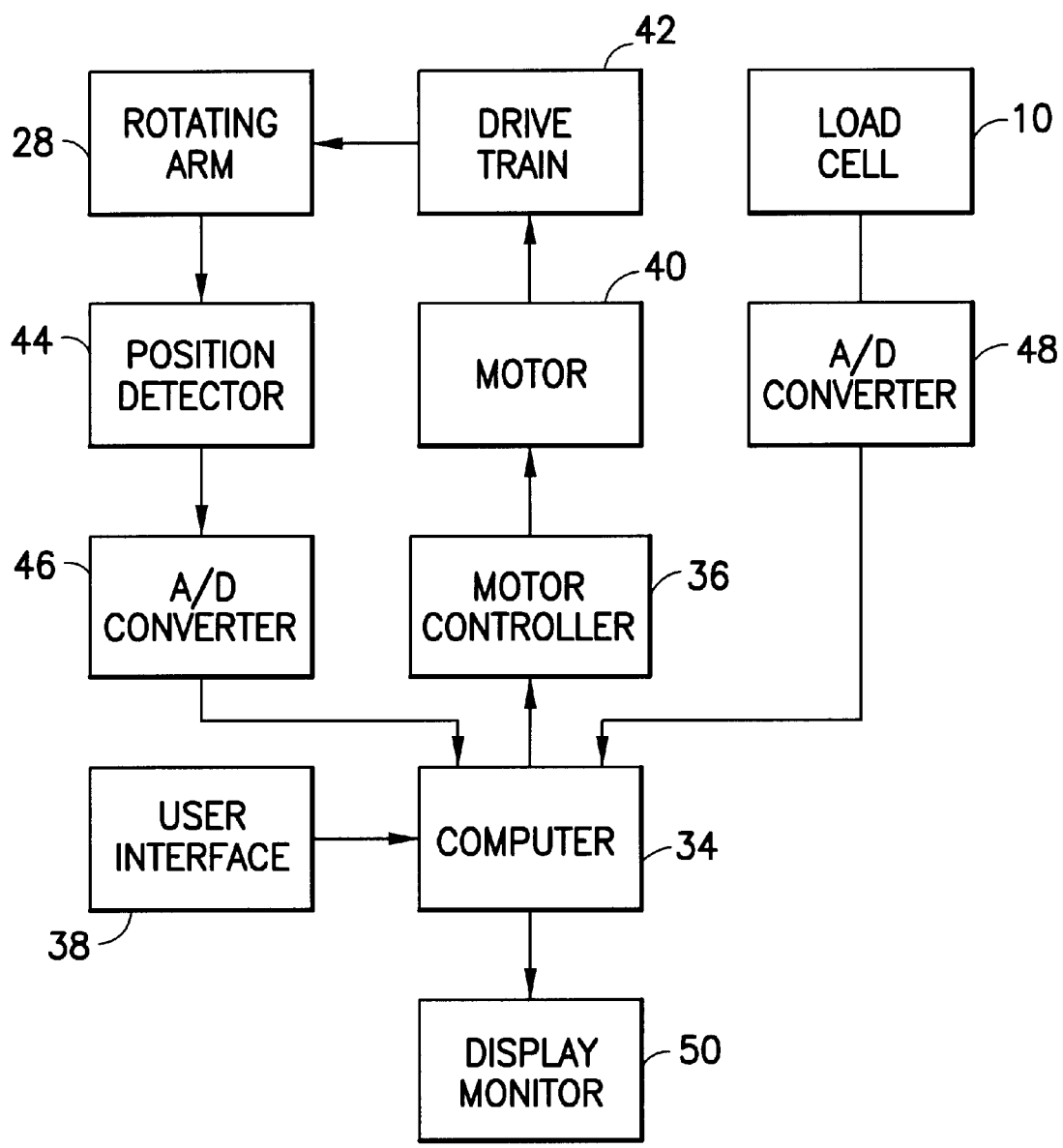
FIG. 12 is a block diagram generally depicting the electrical and some mechanical components of the top-ply fracture tester in accordance with the preferred embodiment of the invention.

A preferred embodiment of the top-ply fracture tester is depicted in FIGS. 10–12. To allow for the gradual material "degradation", i.e. cracking, within the outermost ply, the top-ply fracture tester mechanism has been designed to bend any multi-ply film- or sheet-like structure S, e.g. linerboard, around a ⅛-inch vertical (fixed) spindle 2 (refer to FIG. 10) supported by a spindle support structure 4. In so doing, the sample S will experience a net resultant tensile force. The sample (e.g., 1 inch wide and 5.75 inch long) is firmly held between two air (pneumatic) clamps 6 and 8. The opposing surfaces of the jaws of these air clamps have transverse grooves to ensure no slippage of the paperboard sample S during bending. Air is supplied to the clamps from a pressurized source via air lines 32 by operation of an air supply switch 35.

In accordance with the preferred embodiment, air clamp 6 is fixedly coupled to a load cell 10 via a rod 12. The rod 12 is vertically supported by a mounting bracket 24 attached to the base 30. The load cell 10 is attached to an L-shaped bracket 26, the latter also being mounted to the base 30. The load cell 10 is thus coupled to the air clamp 6 via rod 12 and measures the sample load response during bending.

The other air clamp 8 is mounted to one end of a rod 16. The other end of rod 16 has a spring housing 18 mounted thereto. The rod 16 is slidably supported by a mounting bracket 22 attached to the base 30. Thus the assembly of the air clamp 8, the spring housing 18 and the rod 16 is axially slidable as a unit. A spring 14 is installed inside the spring housing 18 and couples the assembly to a fixed rod 17 which has a radial flange at one end. The spring 14 applies a tensile load to the sample. The rod 17 is fixedly supported by a mounting bracket 20. The rod 17 and a hole in the mounting bracket 20 are both threaded to allow adjustment of the axial position of the rod 17, which in turn allows the operator to adjust the tension applied by spring 14 depending on the basis weight of the material being tested.

The brackets 20 and 22 are both mounted to a rotating or turning arm 28. The turning arm is rotatable about the axis of spindle 2, preferably to a maximum of about 160 degrees. As the turning arm swings, it carries the air clamp 8, causing the latter to rotate about the spindle axis, which in turn causes the sample S to bend around the spindle 2. In FIG. 11, the turning arm 28 is shown in the starting position A and in a rotated position B. As is best seen in FIG. 10, the spindle support structure 4 is mounted to the top of base 30. The turning arm 28 is rotatably mounted to base 30 by means of a bearing (not shown).

Further components of the top-ply fracture tester in accordance with the preferred embodiment are shown in FIG. 12. The turning arm 28 is rotated under the control of a computer 34, which is preferably incorporated in the test stand (as seen in FIG. 10). The computer 34 supplies the appropriate command to a motor controller 36 in response to depression of a "run" key on an operator interface 38. In response to the "run" command from the computer, the motor controller activates an electric motor 40. The electric motor 40 has an output shaft (not shown) which is coupled to the turning arm 28 via a drive train (e.g., a gear assembly) 42. The arm 28 can be set to rotate at varying speeds; for example, successful tests have been conducted with the arm rotational speed set at 1 degree/second. Testing requiring faster rates of elongation may be accommodated by varying the speed of the rotating arm.

As the turning arm 28 rotates, a position detector 44 detects the angular position of the arm and outputs an analog signal. This analog signal is converted to a digital signal by an analog-to-digital converter 46, which sends a digital signal representing arm angular position to the computer 34. At the same time, the load cell 10 measures the tensile force or load being applied to the sample during rotation of the turning arm 28 and outputs an analog signal. This analog signal is converted to a digital signal by another analog-to-digital converter 48, which sends a digital signal representing tensile load to the computer 34. Thus the computer simultaneously acquires tensile load data and angular position (i.e., displacement) data. The computer is programmed to generate a characteristic, real-time load-elongation curve (e.g., of the type shown in FIG. 5) for display on a display monitor 50.

As in tensile testing regimes and the like, the sample's strain rate is critical to the fundamental material properties being recorded. While the board's plastic component of deformation is, for instance, an inherent material property, and hence will be true in all (correct) testing conditions, values will vary for significantly different strain rates. For the preferred top-ply fracture tester design, the strain rate is affected by three factors: the spring load, the arm rotational speed and the gauge length [the distance between the two free edges of the clamps]. It is thus imperative that all measured values be quoted with corresponding rate of elongation, or arm speed. For the example where the sample width was 1 inch wide, sample length was 5.75 inch long, and the arm speed was 1 degree/second, the gauge length was fixed at 4 inches. When in operation, a characteristic, real-time load-elongation curve is obtained. The testing operation and relevant calculations are controlled via a computer program. The test results are displayed on the display monitor and can be output to a printer in response to a print command input via the operator interface.

Using the present invention, an operator is able to correlate material changes in a multi-ply board with "damage" phenomena occurring physically, which are, relatively speaking, easily detectable. When a two-ply linerboard sample is tested as described above, the operator would visually notice three distinct phenomena taking place at three discrete intervals: (1) the development of a (macro) crack as the sample is bent around the spindle; then (2) the opening up of the (macro)crack; and finally (3) the complete separation of the fibers, just prior to eventual failure and delamination of the top ply from the base ply. These crack, gap and flap stages represent the entire zone of plastic deformation while subjecting the top ply to a net tensile state of stress. Plastic deformation in linerboard is thus characterized by two components: the energy consumed during crack-to-gap and that consumed during gap-to-flap (see FIG. 5). Each component, or both, may be optimized to improve certain aspects of the board's ability to deform plastically, and, in turn, resistance to cracking.

The visual detection of the crack, gap and flap is recorded by pressing a respective pre-specified alphanumeric key on the user interface 38, e.g., a keypad, for each event. Once the test is complete, the computer program computes the (elastic and plastic) energies consumed from inception to failure of the single ply. Generally, the following is determined from a specimen's load-elongation curve: (1) energy consumed during elastic deformation (up to crack initiation); (2) energy consumed during crack-to-gap (the first plastic component); (3) energy consumed during gap-to-flap (second plastic component); and (4) energy consumed during crack-to-flap [total plastic contribution, or sum of (2) and (3)]. All of these values are computed along with the standard deviations, which may further help indicate two things: operator's precision (the larger the standard deviation, the worse is the operator's accuracy for recording crack, gap and flap) and sample variability (for instance, the standard deviation tends to be higher for recycle furnishes owing to inherent variability in pulp quality and, hence, mechanical properties of the board). Crack propagation is observed in real-time in the top ply, and as material degradation continues, in the base ply (or succeeding plies, as the case may be).

In accordance with one test procedure, fifteen replicates were tested for each sample. The samples were generally conditioned overnight in a controlled environment of 23±2°C. and 50±5% relative humidity. Testing should preferably be performed in a similarly controlled environment.

In accordance with a further preferred embodiment of the invention, the detection of crack, gap and flap can be automated by the use of acoustics. The working assumption is that each stage of damage accumulation is characterized by a particular pattern of crack propagation, with which is associated a specific rate of bond breakage and/or number of fiber breaks. Technical efforts must concentrate on eliminating noisy activities from regions other than those of interest (i.e., where cracks are propagating), while being able to accurately detect relative sound changes arising at the three distinct stages of damage.

Top-ply fracture testing in accordance with the method disclosed above was performed on a large number of samples of two-ply linerboard. This test data was initially used to validate the inherent properties measured by the top-ply fracture tester vis-à-vis the linerboard's score-line cracking performance in the field. Subsequently, having established the robustness and efficacy of the test, the top-ply fracture tester was utilized as the cornerstone behind improving the functionality (score-line cracking resistance) of a two-ply linerboard. Table 1 summarizes representative results and the concomitant trends.

TABLE 1

| Sample | To Crack (lb-deg) | S.D. | Crack-to-Gap (lb-deg) | Gap-to-Flap (lb-deg) | Crack-to-Flap (lb-deg) | Percent Field Cracking |
|---|---|---|---|---|---|---|
| 1 | 1,591 | 183 | 415 | 511 | 926 | 6.1 |
| 2 | 1,728 | 246 | 424 | 593 | 1,017 | 9.3 |
| 3 | 1,860 | 404 | 664 | 2,102 | 2,766 | 0 |
| 4 | 1,654 | 218 | 615 | 2,611 | 3,227 | 0 |

S.D. is the standard deviation of the energy consumed up to crack initiation. The test data in Table 1 show a clear trend how the propensity for cracking (as quantified by the percent field cracking, which is the crack length percent relative to the length of the score line) correlates with energy consumed during the crack-to-flap transition, or the total energy consumed during plastic deformation. The following factors were found to affect the sheet's ability to plastically deform: the furnish type (virgin versus recycle), furnish quality (e.g. pulp viscosity), degree of fiber development (refining), inter-ply bonding and top-ply coverage. The interacting effects between each, or several of the above factors, result in the development of larger plastic zones of deformation in the top ply.

In conclusion, the top-ply fracture tester disclosed herein measures fundamental properties that show reproducible, accurate correlation with field performance. Using the top-ply fracture tester, one would be able to develop tools that enable the prediction of cracking propensity in terms of inherent material parameters (energy consumption during plastic deformation, or crack-to-flap) and papermaking conditions (that ultimately affect the board's material properties). By balancing the magnitudes of the two plastic components (crack-to-gap and gap-to-flap), one will also be better able to understand the limits to which the papermaking conditions and structural parameters (e.g., top-ply coverage) could be changed if the basic fiber properties (e.g., pulp furnish and/or quality) change, so as to produce optimal cracking-resistant linerboard.

It should also be noted that capabilities to predict score-line cracking propensity must intrinsically be associated with measuring energy absorption in the subject material, specifically, the energy consumed during plastic deformation. Routine mechanical measures (such as tensile strength, TEA, etc.) have been shown not to correlate, as expected from a theoretical standpoint).

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method for predicting score-line cracking propensity of a multi-ply substrate, comprising the steps of:
   bending a sample of a multi-ply substrate;
   acquiring data from said sample during said bending step; and
   computing a material property of a top ply of said sample based at least in part on said acquired data, wherein said material property shows a strong correlation to the score-line cracking propensity of said multi-ply substrate.

2. The method as recited in claim 1, wherein said material property is energy consumed in plastic deformation of said top ply during a fracture process.

3. The method as recited in claim 1, wherein said multi-ply substrate is paperboard.

4. The method as recited in claim 1, further comprising the step of recording a time of crack initiation in said top ply as said sample is bent, wherein said material property is computed based at least in part on said recorded time of crack initiation.

5. The method as recited in claim 4, further comprising the step of detecting an acoustic event which accompanies crack initiation.

6. The method as recited in claim 1, further comprising the step of recording a time of complete separation of fibers in said top ply as said sample is bent, wherein said material property is computed based at least in part on said recorded time of complete separation of fibers.

7. The method as recited in claim 6, further comprising the step of detecting an acoustic event which accompanies complete separation of fibers.

8. The method as recited in claim 1, wherein said acquiring step comprises the step of measuring a tensile load in said sample as said sample is bent.

9. The method as recited in claim 8, wherein said measuring step further comprises the step of producing an analog electrical signal representing tensile load in said sample as said sample is bent.

10. The method as recited in claim 8, wherein said bending step comprises the steps of:
    clamping first and second ends of said sample;
    contacting an intermediate portion of said sample with a spindle; and
    rotating one of said clamped ends about an axis of said spindle while holding the other of said clamped ends fixed.

11. A system for predicting score-line cracking propensity of a multi-ply substrate, comprising:
    means for bending a sample of a multi-ply substrate;
    means for acquiring tensile load data from said sample during bending; and
    means for computing a material property of a top ply of said sample based at least in part on said acquired tensile load data, wherein said material property shows a strong correlation to the score-line cracking propensity of said multi-ply substrate.

12. The system as recited in claim 11, wherein said material property is energy consumed in plastic deformation of said top ply during a fracture process.

13. The system as recited in claim 11, wherein said multi-ply substrate is paperboard.

14. The system as recited in claim 11, further comprising an input device for recording a time of crack initiation in said top ply as said sample is bent, wherein said material property is computed based at least in part on said recorded time of crack initiation.

15. The system as recited in claim 11, further comprising an input device for recording a time of complete separation of fibers in said top ply as said sample is bent, wherein said material property is computed based at least in part on said recorded time of complete separation of fibers.

16. A system for predicting score-line cracking propensity of a multi-ply substrate, comprising:
    a mechanism for bending a sample of a multi-ply substrate;
    an instrument for acquiring data from said sample during bending; and
    a computer programmed to compute a material property of a top ply of said sample based at least in part on said acquired data, wherein said material property shows a strong correlation to the score-line cracking propensity of said multi-ply substrate.

17. The system as recited in claim 16, wherein said material property is energy consumed in plastic deformation of said top ply during a fracture process.

18. The system as recited in claim 16, wherein said multi-ply substrate is paperboard.

19. The system as recited in claim 16, further comprising an input device for recording a time of crack initiation in said top ply as said sample is bent, wherein said material property is computed based at least in part on said recorded time of crack initiation.

20. The system as recited in claim 16, further comprising an input device for recording a time of complete separation of fibers in said top ply as said sample is bent, wherein said material property is computed based at least in part on said recorded time of complete separation of fibers.

21. The system as recited in claim 16, wherein said instrument comprises a load cell arranged to measure a tensile load in said sample as said sample is bent.

22. The system as recited in claim 21, further comprising an analog-to-digital converter for converting an analog electrical signal output by said load cell into a digital signal which is output to said computer.

23. The system as recited in claim 21, wherein said mechanism comprises:
    a fixed spindle having an axis;
    a first clamp for clamping one end of said sample, said first clamp being fixed at a predetermined distance from said spindle and coupled to said load cell;
    a second clamp for clamping the other end of said sample, said second clamp being movable along an arc substantially centered at said spindle axis; and
    a drive mechanism for causing said second clamp to travel along said arc.

24. The system as recited in claim 23, wherein each of said first and second clamps comprises a pneumatic clamp.

25. A method for predicting score-line cracking propensity of a multi-ply paperboard, comprising the steps of:
    bending a sample of a multi-ply paperboard;
    acquiring tensile load data from said sample during said bending step; and computing the energy consumed in plastic deformation of a top ply of said sample during a fracture process based at least in part on tensile load data acquired during said acquiring step wherein said energy consumed shows a strong correlation to the score-line cracking propensity of said multi-ply paperboard.

26. The method as recited in claim 25, wherein said fracture process comprises a crack-to-gap transition.

27. The method as recited in claim 25, wherein said fracture process comprises a gap-to-flap transition.

28. The method as recited in claim 25, further comprising the step of computing a standard deviation of said energy consumed in plastic deformation of said top ply of said sample.

* * * * *